United States Patent
Eroshenko et al.

(10) Patent No.: US 9,777,262 B2
(45) Date of Patent: Oct. 3, 2017

(54) MUTANTS OF CRE RECOMBINASE

(71) Applicant: President and Fellows of Harvard College, Cambridge, MA (US)

(72) Inventors: Nikolai A. Eroshenko, Boston, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/774,319

(22) PCT Filed: Feb. 26, 2014

(86) PCT No.: PCT/US2014/018607
§ 371 (c)(1),
(2) Date: Sep. 10, 2015

(87) PCT Pub. No.: WO2014/158593
PCT Pub. Date: Oct. 2, 2014

(65) Prior Publication Data
US 2016/0017298 A1    Jan. 21, 2016

Related U.S. Application Data

(60) Provisional application No. 61/778,808, filed on Mar. 13, 2013.

(51) Int. Cl.
| C12N 15/09 | (2006.01) |
| C07K 14/005 | (2006.01) |
| C12N 15/90 | (2006.01) |
| C12N 9/12 | (2006.01) |
| C12N 9/00 | (2006.01) |
| C12P 19/34 | (2006.01) |

(52) U.S. Cl.
CPC ............ *C12N 9/1241* (2013.01); *C12N 9/00* (2013.01); *C12P 19/34* (2013.01); *C12Y 207/07* (2013.01)

(58) Field of Classification Search
None
See application file for complete search history.

(56) References Cited

U.S. PATENT DOCUMENTS

| 6,890,726 B1 | 5/2005 | Sauer et al. |
| 2012/0331574 A1 | 12/2012 | Arnould et al. |
| 2013/0059387 A1 | 3/2013 | Smith et al. |

OTHER PUBLICATIONS

Mienke et al. Cre Recombinase and Other Tyrosine Recombinases. Chem. Rev. 2016. 12785-12820.*
Karimova et al. Vika/Vox, A Novel Efficient and Specific Cre/loxP-like Site-Specific Recombination System. Nucleic Acids Research, 2012. 1-13.*
Shaikh and Sadowski. Trans Complementation of Variant Cre Proteins for Defects and Synapsis. The Journal of Biological Chemistry, 2000. 275(39):30186-30195.*
Office Action issued for corresponding European Patent Application No. 14773467.7, dated Nov. 3, 2015.
International Search Report issued from corresponding PCT/US14/18607, dated May 20, 2014.
Eroshenko et al., Mutants of Cre recombinase with improved accuracy. Nat Commun. 23 Sep. 1-10, 2013, vol. 4, Article No. 2509, pp. 1-21.
Wunderlich et al., New variants of inducible Cre recombinase: a novel mutant of Cre-PR fusion protein exhibits enhanced sensitivity and an expanded ~:ange of inducibility. Nucleic Acids Res, May 15, 2001, vol. 29, No. 10, pp. e47.

* cited by examiner

*Primary Examiner* — Christopher M Babic
*Assistant Examiner* — Kimberly A Aron
(74) *Attorney, Agent, or Firm* — Banner & Witcoff, Ltd.

(57) ABSTRACT

The present invention relates to mutants of Cre recombinase.

7 Claims, 7 Drawing Sheets

```
       loxP ATAACTTCGTATA ATGTATGC TATACGAAGTTAT
    loxBait ATAACTTCGTATA ATGTATGC TAACTATACGTCG
  ψLox h7q21 ATATATATGTATA TATACATA TATACGTATGTAT
 ψCore h7q21 ATAACTTCGTATA TATGTATA TATACGAAGTTAT
```

FIG. 2

SEQUENCE LISTING

```
<160> NUMBER OF SEQ ID NOS: 19

<210> SEQ ID NO 1
<211> LENGTH: 34
<212> TYPE: DNA
<213> ORGANISM: Artificial
<220> FEATURE:
<223> OTHER INFORMATION: oligonucleotide sequence

<400> SEQUENCE: 1
ataacttcgt ataatgtatg ctatacgaag ttat                              34

<210> SEQ ID NO 2
<211> LENGTH: 34
<212> TYPE: DNA
<213> ORGANISM: Artificial
<220> FEATURE:
<223> OTHER INFORMATION: oligonucleotide sequence

<400> SEQUENCE: 2
```
ataacttcgt ataatgtatg ctaactatac gtcg                34

<210> SEQ ID NO 3
<211> LENGTH: 34
<212> TYPE: DNA
<213> ORGANISM: Artificial
<220> FEATURE:
<223> OTHER INFORMATION: oliginucleotide sequence

<400> SEQUENCE: 3
atatatatgt atatatacat atacgtat gtat                  34

<210> SEQ ID NO 4
<211> LENGTH: 34
<212> TYPE: DNA
<213> ORGANISM: Artificial
<220> FEATURE:
<223> OTHER INFORMATION: oligonucleotide sequence

<400> SEQUENCE: 4
ataacttcgt atatatgtat atacgaag ttat                  34

<210> SEQ ID NO 5
<211> LENGTH: 34
<212> TYPE: DNA
<213> ORGANISM: Artificial
<220> FEATURE:
<223> OTHER INFORMATION: oligonucleotide sequence

<400> SEQUENCE: 5
ataacttcgt ataatgtatg ctatacaaag taat                34

<210> SEQ ID NO 6
<211> LENGTH: 34
<212> TYPE: DNA
<213> ORGANISM: Artificial
<220> FEATURE:
<223> OTHER INFORMATION: oligonucleotide sequence

<400> SEQUENCE: 6
ataacttcgt ataatgtatg ctatagagag taat                34

<210> SEQ ID NO 7
<211> LENGTH: 34
<212> TYPE: DNA
<213> ORGANISM: Artificial
<220> FEATURE:
<223> OTHER INFORMATION: oligonucleotide sequence

<400> SEQUENCE: 7
ataacttcgt ataatgtatg ctatccttaa ttat                34

<210> SEQ ID NO 8
<211> LENGTH: 34
<212> TYPE: DNA
<213> ORGANISM: Artificial
<220> FEATURE:
<223> OTHER INFORMATION: oligonucleotide sequence

<400> SEQUENCE: 8
ataacttcgt ataatgtatg ctatcggtag tcac                34

<210> SEQ ID NO 9
<211> LENGTH: 34
<212> TYPE: DNA
<213> ORGANISM: Artificial

```
<220> FEATURE:
<223> OTHER INFORMATION: oligonucleotide sequence

<400> SEQUENCE: 9
ataacttcgt ataatgtatg ctttacacat taat                                34

<210> SEQ ID NO 10
<211> LENGTH: 34
<212> TYPE: DNA
<213> ORGANISM: Artificial
<220> FEATURE:
<223> OTHER INFORMATION: oligonucleotide sequence

<400> SEQUENCE: 10
ataacttcgt ataatgtatg ctatgctcag tgat                                34

<210> SEQ ID NO 11
<211> LENGTH: 34
<212> TYPE: DNA
<213> ORGANISM: Artificial
<220> FEATURE:
<223> OTHER INFORMATION: oligonucleotide sequence

<400> SEQUENCE: 11
ataacttcgt ataatgtatg ctatttttag tcaa                                34

<210> SEQ ID NO 12
<211> LENGTH: 34
<212> TYPE: DNA
<213> ORGANISM: Artificial
<220> FEATURE:
<223> OTHER INFORMATION: oligonucleotide sequence

<400> SEQUENCE: 12
ataacttcgt ataatgtatg cgatactact ataa                                34

<210> SEQ ID NO 13
<211> LENGTH: 34
<212> TYPE: DNA
<213> ORGANISM: Artificial
<220> FEATURE:
<223> OTHER INFORMATION: oligonucleotide sequence

<400> SEQUENCE: 13
ataacttcgt ataatgtatg ctatgggcta gcaa                                34

<210> SEQ ID NO 14
<211> LENGTH: 34
<212> TYPE: DNA
<213> ORGANISM: Artificial
<220> FEATURE:
<223> OTHER INFORMATION: oligonucleotide sequence

<400> SEQUENCE: 14
ataacttcgt ataatgtatg ctaactagat gtac                                34

<210> SEQ ID NO 15
<211> LENGTH: 34
<212> TYPE: DNA
<213> ORGANISM: Artificial
<220> FEATURE:
<223> OTHER INFORMATION: oligonucleotide sequence

<400> SEQUENCE: 15
ataacttcgt ataatgtatg cttatcgaat ctat                                34
```

```
<210> SEQ ID NO 16
<211> LENGTH: 34
<212> TYPE: DNA
<213> ORGANISM: Artificial
<220> FEATURE:
<223> OTHER INFORMATION: oligonucleotide sequence

<400> SEQUENCE: 16
ataacttcgt ataatgtatg ctaactatac gtcg                                34

<210> SEQ ID NO 17
<211> LENGTH: 34
<212> TYPE: DNA
<213> ORGANISM: Artificial
<220> FEATURE:
<223> OTHER INFORMATION: oligonucleotide sequence

<400> SEQUENCE: 17
ataacttcgt ataatgtatg ctatctaccg tctg                                34

<210> SEQ ID NO 18
<211> LENGTH: 34
<212> TYPE: DNA
<213> ORGANISM: Artificial
<220> FEATURE:
<223> OTHER INFORMATION: oligonucleotide sequence

<400> SEQUENCE: 18
ataacttcgt ataatgtatg cattgacaaa caga                                34

<210> SEQ ID NO 19
<211> LENGTH: 34
<212> TYPE: DNA
<213> ORGANISM: Artificial
<220> FEATURE:
<223> OTHER INFORMATION: oligonucleotide sequence

<400> SEQUENCE: 19
ataacttcgt ataatgtatg cataaatttt atag                                34
```

MUTANTS OF CRE RECOMBINASE

RELATED APPLICATION DATA

This application claims priority to U.S. Provisional Patent Application No. 61/781,373 filed on Mar. 14, 2013 and is hereby incorporated herein by reference in its entirety for all purposes.

STATEMENT OF GOVERNMENT INTERESTS

This invention was made with government support under grant number N00014-10-1044 awarded by the Office of Naval Research (ONR) Multidisciplinary University Research Initiative (MURI) and grant number 1P50 HG005550 awarded by the NIH P50 Centers in Excellence in Genomic Science (CEGS). The Government has certain rights in the invention.

FIELD

The present invention relates in general to mutants of Cre recombinase resulting in improved accuracy.

BACKGROUND

Safe delivery of transgenes into the human genome remains an open problem of critical importance to clinical genetics. Many existing technologies have major limitations. For instance, retroviruses, lentiviruses, and transposons integrate non-specifically and can therefore cause cancer by mutagenesis[1-3]. Transgenes can also be integrated using the endogenous homologous repair pathways, although this process must be stimulated by generating double-stranded breaks at the target site using programmable nucleases technologies such as meganucleases[4,5], zinc finger nucleases[6], TALE nucleases[7,8], or the RNA-guided Cas9 protein[9,10]. This technique is limited by the fact that homologous recombination in humans is less efficient than the competing mutagenic nonhomologous end joining pathway[11,12].

Site-specific recombinases, which catalyze recombination at precise sites, have properties that make them promising candidates for use as safe gene delivery vectors. For instance, many of them require no host-encoded factors for function[13]. The size of the integrated cassette is less restricted than for other methods. The sequence specificity, i.e. the intended binding site of a protein, of recombinases can be altered either by direction evolution or by fusing them to modular DNA-binding domains[14-23]. Unfortunately, many reprogrammed variants are promiscuous in their activity. This problem isn't restricted to artificial variants, as activity at off-target human genomic loci has been reported for some wild-type (WT) recombinases[24-29]. If recombinases are to be used as gene delivery vectors it is imperative to identify ways to enhance their accuracy.

One way to improve the accuracy of DNA-binding proteins is to increase the number of specific or decrease the number of non-specific DNA-protein contacts[30,31]. While powerful, this approach can be inconvenient if the goal is to generate variants of a protein with different specificities: a specificity change would alter the DNA-protein interaction, requiring re-optimization of accuracy. There is therefore a need for ways to systematically enhance accuracy without altering the DNA-protein interface.

Cre catalyzes a reversible, directional recombination between two 34 base-pair (bp) loxP sequences named which consist of a pair of 13 bp inverted repeats flanking a 8 bp asymmetrical spacer[32-35]. Mutagenic studies of loxP have shown that many mutations have non-catastrophic effects on recombination efficiency[36-38].

SUMMARY

The present disclosure uses superscripts to reference documents which are listed at the end of the present disclosure. The document corresponding to the superscript is incorporated by reference into the specification as a supporting reference corresponding to the superscript as if fully cited.

Embodiments of the present disclosure are directed to mutants of Cre recombinase which have improved accuracy and directionality of catalysis. According to one aspect, the mutations are outside of the DNA-protein interface. According to one aspect, the mutations are in the dimerization surface of Cre recombinase. According to one aspect, the mutations are one or more of R32V, R32M, and 303GVSdup. According to one aspect, methods are provided for destabilizing the cooperative binding of DNA-binding proteins in a manner to improve their accuracy. According to one aspect, methods are provided to reduce the toxicity of Cre-based animal and tissue models by using the mutant Cre recombinases described herein. According to one aspect, methods are provided to simplify directed evolution of novel specificities by using the mutant Cre recombinases described herein.

According to embodiments described herein, Cre recombinase of the phage P1 is used as a model system. Mutants of Cre recombinase described herein are capable of efficiently recombining on-target sites but with a reduced efficiency on off-target sites. According to certain aspects, a region involved in the formation of Cre dimers was mutagenized and bacterial selections for functional and accurate mutants was performed. Mutants are isolated which were able to recombine loxP sites with high efficiency and exhibited improved accuracy with respect to both a model human off-target site as well as the entire E. coli genome.

BRIEF DESCRIPTION OF THE DRAWINGS

The foregoing and other features and advantages of the present invention will be more fully understood from the following detailed description of illustrative embodiments taken in conjunction with the accompanying drawing in which:

FIG. 2 are sequences depicting recombination sites (SEQ ID NO. 1, SEQ ID NO. 2, SEQ ID NO. 3, and SEQ ID NO. 4).

DETAILED DESCRIPTION

Figure 1:
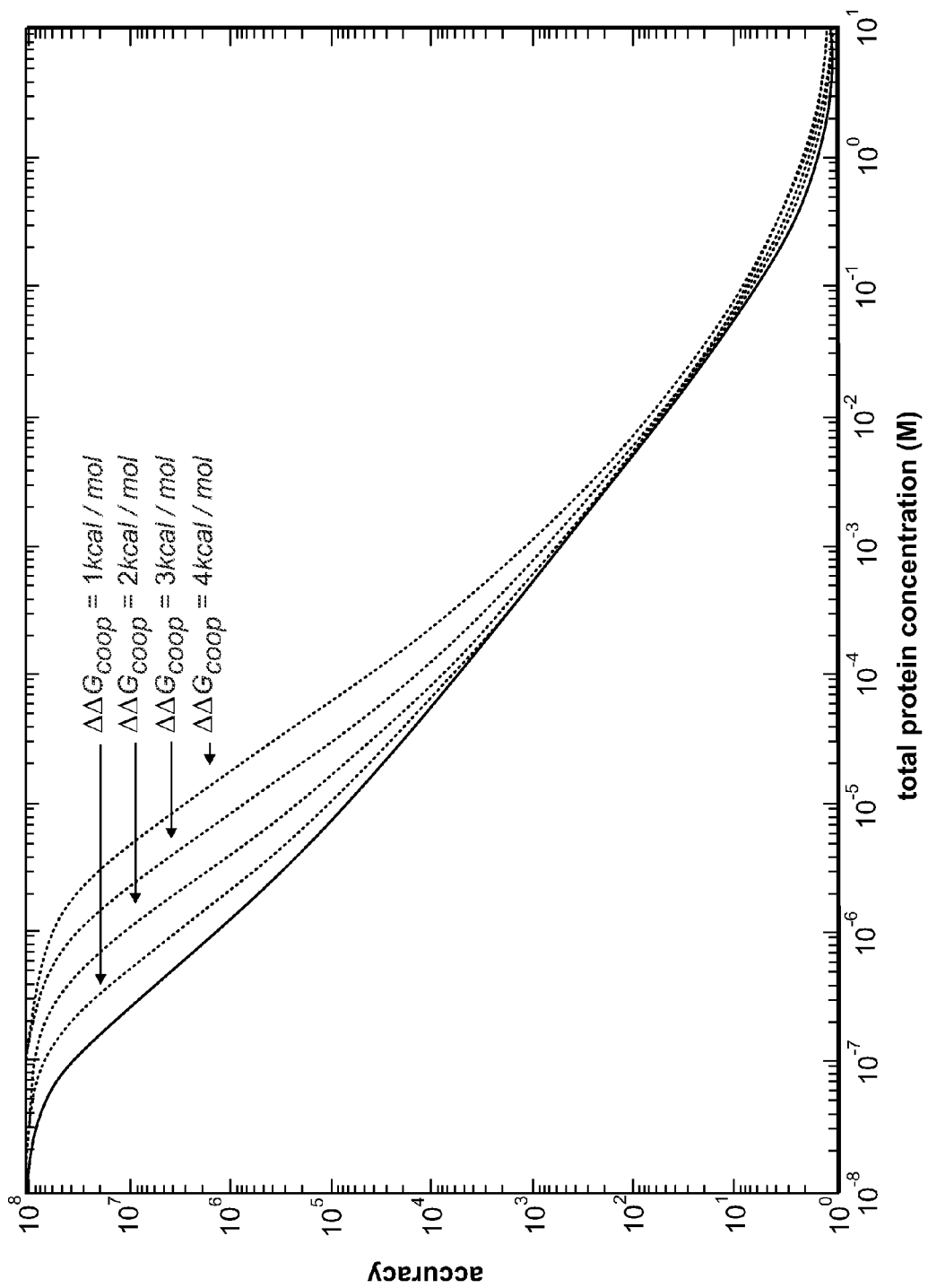
FIG. 1 is graph of accuracy versus total protein concentration.

This present disclosure is directed to mutants of Cre recombinase having increased activity. According to one aspect, mutants of the present disclosure include R32V, R32M, and 303GVSdup. According to one aspect, a method is provided including the use of the mutants described herein to recombine loxP with desirable efficiency. According to one aspect, a method is provided including the use of the mutants described herein having better directionality compared to WT. According to one aspect, a method is provided including the use of the mutants described herein having better accuracy with respect to the human genome off-target site φLox h7q21. According to one aspect, a method is provided including the use of the mutants described herein having better accuracy with respect to the entire E. coli genome.

Known structural data strongly suggest that R32V and R32M disrupt a strong salt-bridge in the dimer interface (FIG. 4a). As for 3030GVSdup, an isolated spontaneous mutation occurred at the dimer interface. Given that the mutations do not lie in proximity to the DNA and their high efficiency of loxP recombination described herein, the interaction between Cre monomers and loxP has not been significantly affected. Accordingly, one aspect of the present disclosure the enhanced accuracy of all three mutants during directed evolution of novel specificities is maintained.

Embodiments of the present disclosure utilize cooperativity of DNA-binding as a parameter in the accuracy of DNA-modifying enzymes. Modulation of cooperativity may be useful for reducing off-target activities of other families of proteins such as nucleases, the toxicity of which has been shown to be correlated with specificity of binding[43]. One aspect of this approach is that it decreases on-target affinity. Strong monomer affinities, such as the 1-10 nM Kd of Cre for half of loxP[39,44] are desirable. Weakening cooperativity should be compatible with the two other major strategies of improving accuracy: changing the ratio of specific to non-specific protein-DNA contacts[30,31], and, in the case of heterogenous DNA recognition sites, introduction of heterodimeric protein dimer interfaces[45,46].

Cre makes frequent deletions on a substrate containing inverted loxP[47], and non-matching spacers will occasionally successfully recombine[37,38]. This looseness in directionality of recombination may interfere with synthetic circuit designs that rely on Cre-mediated inversion as a form of genetic memory[48,49]. The three Cre mutants described herein have an improved directionality over WT, and are useful in synthetic biology applications.

Due to its high efficiency and the lack of necessary co-factors Cre is useful in animal genetics[50-52]. However, Cre toxicity in the absence of loxP sites has been observed in a number of animal and cell culture systems[53-62]. The source of this toxicity is not known. However, a number of observations, including the absence of toxicity from catalytically inactive Cre mutants, the increased frequency of chromosomal rearrangements, Cre's capacity to form stable Holiday Junction intermediates on off-target sites, and evidence of activation of DNA damage response pathways all point at recombination at off-target pseudo-loxP sites as the cause[29,53,55,56,62,63]. Accordingly, embodiments of the present disclosure are directed to Cre mutants that reduce or otherwise alleviating the toxic phenotypes caused by Cre. This should be compatible with existing strategies for reducing Cre toxicity, which include placing the Cre gene in a self-excisable cassette, regulating Cre activity with a hormone binding domain of a steroid receptor, or using a drug-regulated fragment complementation strategy[56,64-66].

According to certain embodiments, one mechanism of Cre recombination is that: 1) Cre binds to one half of the loxP site; 2) a second Cre molecule binds to the other half of loxP, forming an asymmetrical homodimer; 3) a tetramer is formed from the association of two loxP-bound dimers; 4) tetramerization allosterically activates the Cre catalytic sites; and 5) recombination proceed via two strand exchange steps via a Holiday Junction intermediate[35]. The last step occurs strictly on the same DNA molecule is the formation of Cre dimers. According to certain embodiments, the formation of the dimer of dimers is not site specific in the sense that it involves no new DNA binding events. According to this aspect, accuracy is determined by the precision of dimer formation.

Dimer formation on target sites is described with:

$$P + D \overset{2K}{\leftrightarrow} P \cdot D \quad (1)$$

$$P + P \cdot D \overset{K_{dim}}{\longleftrightarrow} 2P \cdot D \quad (2)$$

where P is the unbound protein monomer, D is the full DNA binding sites, K is the affinity of each monomer for half of the binding site, and Kdim is the affinity of the protein dimer for the full binding site. If it is assumed that the cooperative energy is sequence independent then Kdim=KKcoop, where Kcoop is the protein-protein affinity. A competing set of binding events occurs between off-target DNA and the protein:

$$P + D_{OT} \overset{2K_{OT}}{\longleftrightarrow} P \cdot D_{OT} \quad (3)$$

$$P + P \cdot D_{OT} \overset{K_{OT}K_{coop}}{\longleftrightarrow} 2P \cdot D_{OT} \quad (4)$$

where DOT is the off-target DNA concentration and KOT is the affinity of the protein for off-target DNA.

Accuracy can be defined as the ratio of on-target and off-target occupancies, where occupancy is the fraction of all sites occupied by a dimer:

$$A \triangleq \frac{\left(\frac{[2P \cdot D]}{[D] + [P \cdot D] + [P \cdot D]}\right)}{\left(\frac{[2P \cdot D_{OT}]}{[D_{OT}] + [P \cdot D_{OT}] + [2P \cdot D_{OT}]}\right)} \quad (5)$$

This expression can be reduced to:

$$A = \left(\frac{K}{K_{OT}}\right)^2 \left(\frac{K_{coop}K_{OT}^2[P]^2 + K_{OT}[P] + 1/2}{K_{coop}K^2[D]^2 + K[D] + 1/2}\right) \quad (6)$$

[P] can be determined given total protein concentration [Ptot]:

$$[P_{tot}]=2([2P \cdot D]+[2P \cdot D_{OT}])+[P \cdot D]+[P \cdot D_{OT}]+[P] \quad (7)$$

Using the equilibrium relationships (1)-(4) this expression can be rewritten as:

$$0=4K_{coop}(K^2[D]+K_{OT}^2[D_{OT}])[P]^2+(2K[D]+2K_{OT}+1)[P]-[P_{tot}] \quad (8)$$

which is a second degree polynomial with respect to [P] that that be solved with the quadratic formula.

To model accuracy of Cre in *E. coli*, in vitro affinity coefficients K of $1.5 \times 108$ M-1 and a Kcoop of $1.7 \times 103$ M-1 were used with both values obtained from previous in vitro measurements[39]. It was assumed that K/KOT=104, which is in the same order of magnitude as the experimentally determined K/KOT of EcoRV and BamHI[40]. It is to be understood that K/KOT is only an estimation taking into consideration that the recognition site of Cre is larger than that of the restriction enzymes. Assuming a single on-target site in an *E. coli* cell of a 0.5 μm radius gives a [D] of $2.2 \times 10$-9 M. Assuming off-target sites exist at 1 bp windows along both strands of the 4.6 Mbp *E. coli* genome, then [DOT]=$2.2 \times 10$-9 M/bp*9.2e6 bp=2e-2 M. The presence of other protein on the genome as well as higher-order structure may be factored into an estimation of the effective concentration.

The predicted accuracy of dimer formation as a function of total protein concentration for both WT Cre and for mutants with reduced cooperativity was plotted in FIG. 1 which depicts data relating to a model predicting an increase in Cre recombinase dimer binding accuracy with a decrease in cooperativity. The solid line indicates the accuracy predicted for WT Cre, while the dashed lines correspond to the expected accuracy of mutants in which the energy in the protein-protein interface has been reduced by the indicated amount.

Three conclusions can be drawn from this model: 1) accuracy decreases with increasing protein expression levels; 2) accuracy increases a reduction in cooperativity; and 3) if cooperativity is reduced, accuracy improvements will be largest at low protein levels. The second point is consistent given that accuracy should increase when the two monomer binding events become more independent from each other. Accordingly, a reduction in cooperatively will affect both on-target and off-target binding and off-target binding would be destabilized more.

FIG. 2 depicts recombination sites used in the present disclosure. Positions that are different from loxP are shown in bold.

Figure 6:
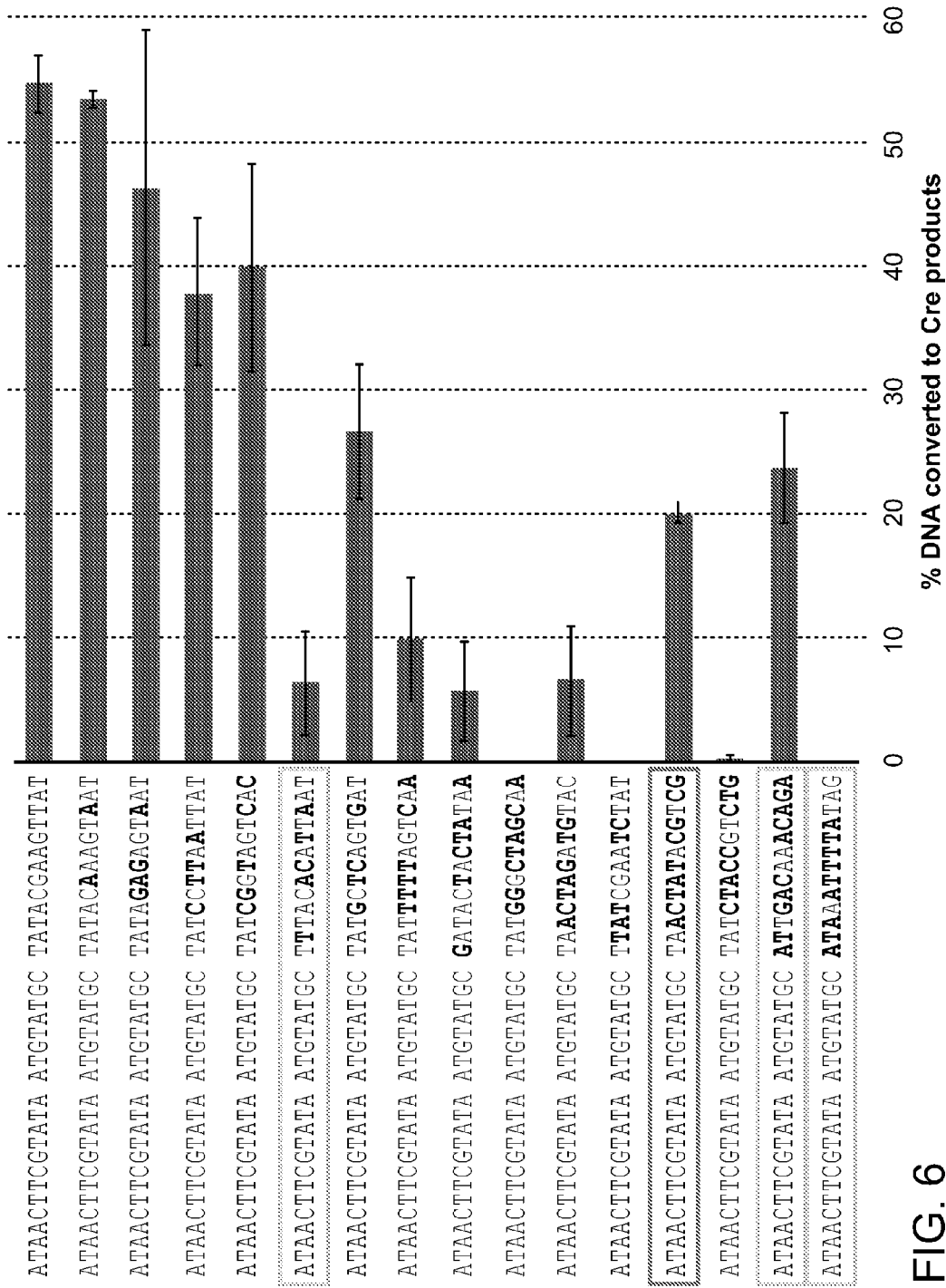
FIG. 6 depicts in vitro recombination efficiency of mutant loxP sites (SEQ ID NO. 1, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, and SEQ ID NO. 19).

FIG. 6 depicts in vitro recombination efficiency of mutant loxP sites. Large linear fragments with loxP on one end and the indicated sites on the other were treated with Cre and the products were quantified on an agarose gel. All new bands were counted towards the recombination efficiency. No recombination was observed for any of the sites in the absence of Cre. Positions indicated in bold correspond to differences from loxP. Sites are provided in order of homology with loxP, with the topmost site being loxP. Green boxes indicate sequences generated randomly (all others were obtained from a selection for functional sites). The blue box marks loxBait, the sequence used in the negative selection of accurate Cre variants. Error bars correspond to 95% C.I. (n=2-3 experimental replicates).

Figure 3:
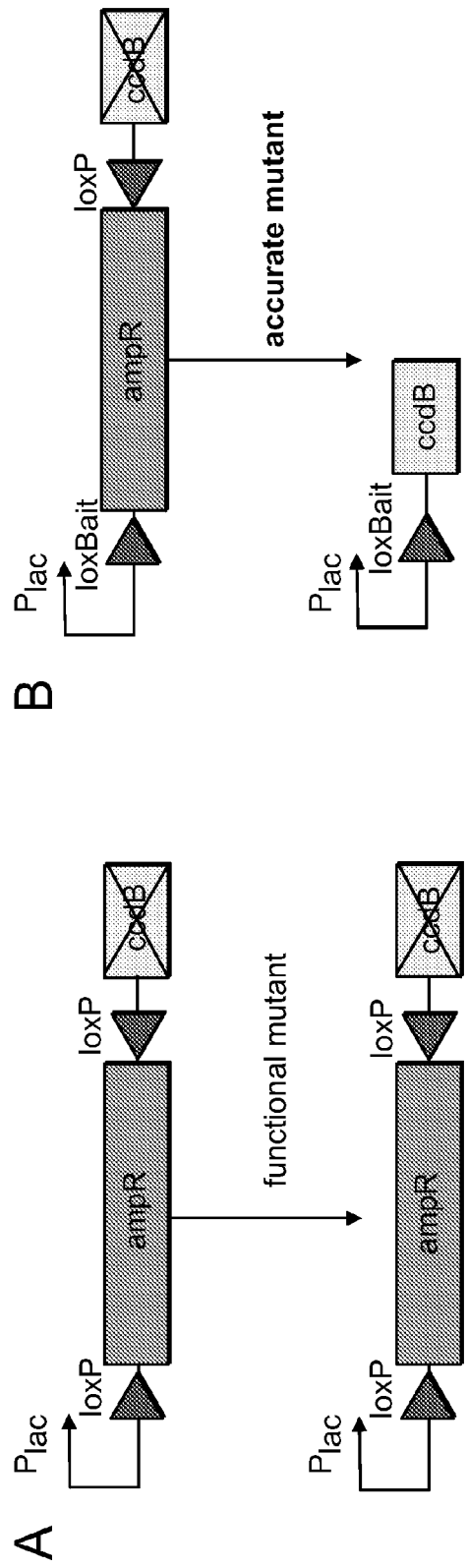
FIG. 3A is a schematic depicting a substrate used to select for functional variants.
FIG. 3B is a schematic depicting a substrate used to select for accurate variants.
FIG. 3C is a graph of the ratio of ampicillin resistant to ampicillin sensitive colonies isolated from position selection.
FIG. 3D is a graph of the number of ampicillin resistant colonies recovered from negative selection.
Figure 3:
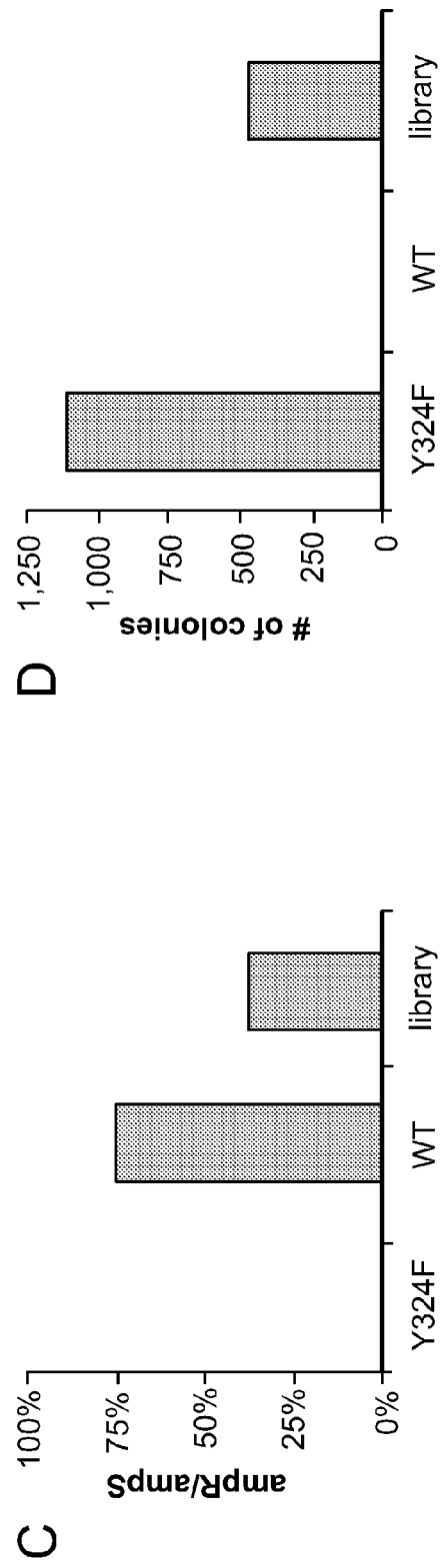

FIG. 3 depicts selection for functional Cre variants and counter-selection against inaccurate variants. As shown in FIG. 3A, the substrate used to select for functional variants—proper recombination would place the ampicillin resistance gene (ampR) under the lac promoter (Plac) conferring resistance. The ccdB gene is crossed out because it is out of frame with respect to the ampR start codon. As shown in FIG. 3B, the substrate used to select for accurate variants—recombination of loxP and loxBait sites would result in loss of ampicillin resistance and would place the toxic ccdB gene in frame with the promoter. FIG. 3C depicts the ratio of ampicillin resistant to ampicillin sensitive colonies isolated from the positive selection. FIG. 3D depicts the number of ampicillin resistant colonies recovered from the negative selection.

Candidate mutations were identified using bacterial selections. According to the present disclosure, accuracy can be improved by decreasing the cooperative binding moment. Mutagenesis was targeted towards a domain directly involved in the dimer interaction but distant from the Cre-DNA interaction: the alpha helix closest to the amino-terminus[41,42]. To find mutations that improve accuracy while maintaining proper function with respect to loxP, two rounds of bacterial selection were performed. The first round was designed to identify functional mutants while the second round selected accurate mutants. To select functional mutants, a resistance marker flanked by loxP sites in inverted orientation relative to each other was used. The reading frame was inverted with respect to the promoter such that Cre-mediated inversion would result in gain of antibiotic resistance (FIG. 3A). To minimize false negatives due to reversal of the inversion, the selection cassette was placed on a high copy plasmid. The selection resulted in the recovery of 1,690 library-transformed colonies or 38% of the total transformation efficiency. This corresponded to fewer clones than were recovered with the positive WT control, suggesting that the selection as functional (FIG. 3C).

To identify accurate constructs, an off-target site was first identified to serve as bait in the negative selection. To achieve a high selective pressure, the bait sequence is intended to recombine with a high efficiency. In order to select for improved accuracy across the entire protein-DNA interaction, the bait is selected to have little sequence similarity to loxP. A site was identified by performing a selection for pseudo-loxP sites and characterizing their in vitro recombination efficiency. The site, identified as lox-Bait, is recombined with 37% the efficiency of *loxP* despite differences in 9 out of 13 bases within a single inverted repeat (FIG. 2 and FIG. 6).

Counter-selection was performed by flanking an in-frame antibiotic resistance marker with loxBait and loxP oriented in the same direction. The toxic ccdB gene was placed 3' of loxP. Cre-mediated excision would result in both loss of the resistance marker and expression of the toxic gene (FIG. 3b). The expression plasmids recovered from the positive selection were subjected to one round of counter-selection. In this case the catalytically inactive mutant, Y324F, served as the control for growth without selection (FIG. 3d).

Figure 4:
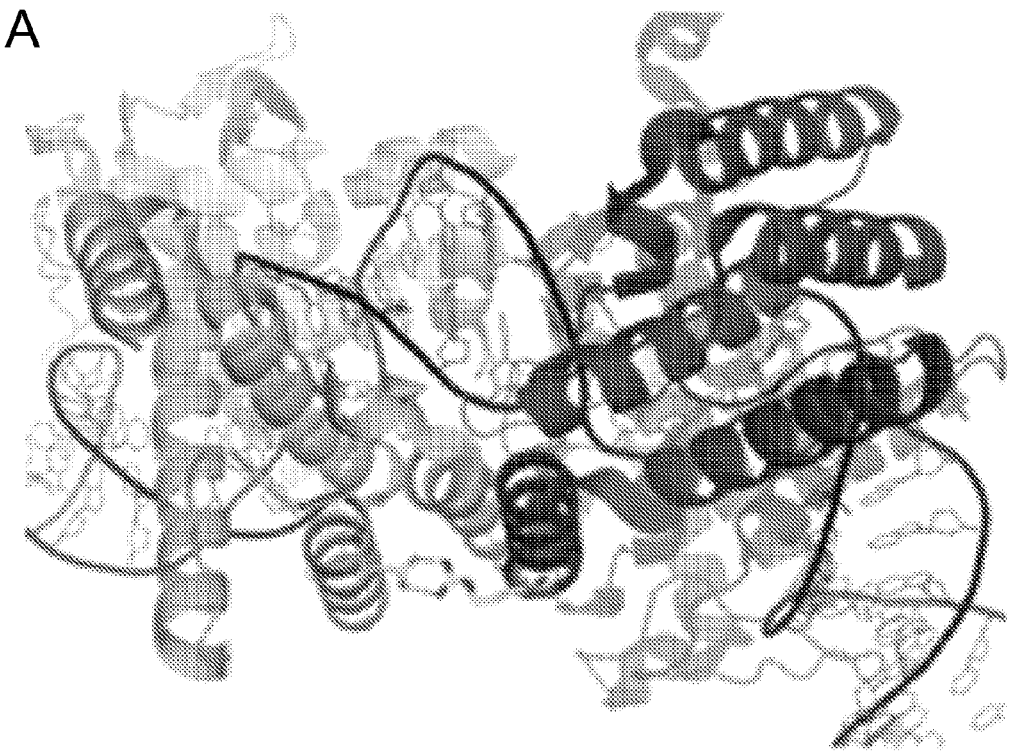
FIG. 4A depicts mutants R32V and R32M.
FIG. 4B depicts mutant 303GVSdup.
Figure 4:
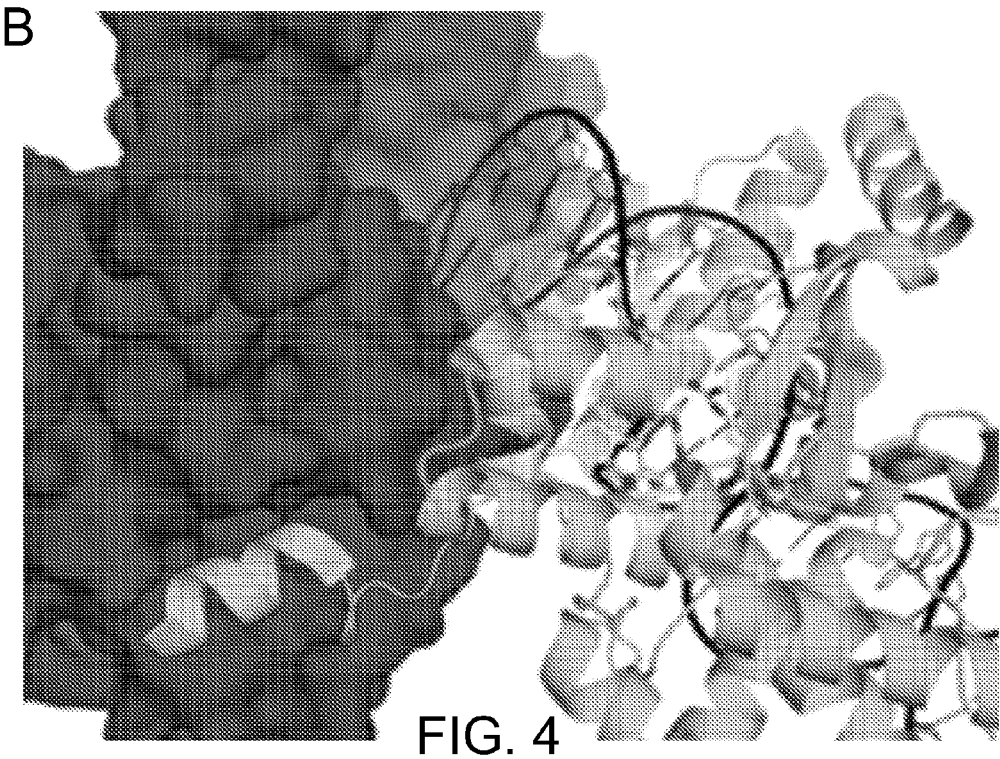

FIG. 4 depicts structural context of the isolated mutants. In FIG. 4A, R32V and R32M disrupt a putative salt bridge between two monomers (shown in blue and green) at R32 and E69. The two residues are shown as stick structures colored by atom identity (blue—N; red—O; gray—C). In FIG. 4B, 303GVSdup duplicated the loop shown in orange. One of the monomers is shown as a space-filling model. The catalytic site residues (R173, H289, R292, W315, Y324) are shown as stick figures. The crystallographic data was obtained from PDB 2CRX[42].

Two of the recovered mutants—R32V and R32M—were randomly isolated for further characterization. The R32 is involved in an inter-monomer salt bridge with E69, so its disruption in the two mutants can be expected to reduce the protein-protein affinity (FIG. 4A). Two WT colonies survived the counter-selection, of which one contained a clone with a de novo duplication of residues 303-305 (303GVS-dup). This region is a loop that makes close contact to the other monomer in the dimer structure (FIG. 4B).

According to methods described herein, R32V, R32M, and 303GVSdup are better able distinguish loxP and a human off-target site. The activity of Cre and the isolated mutants on loxP and φLox h7q21, a known human off-target site[24], were measured using a plasmid-based inversion assay. As in the selections, the proteins were expressed from the Pbad promoter. Cells were grown on repressive LB/glucose medium. Indistinguishable results were achieved with growth on LB in the absence of glucose (data not shown).

Figure 5A:
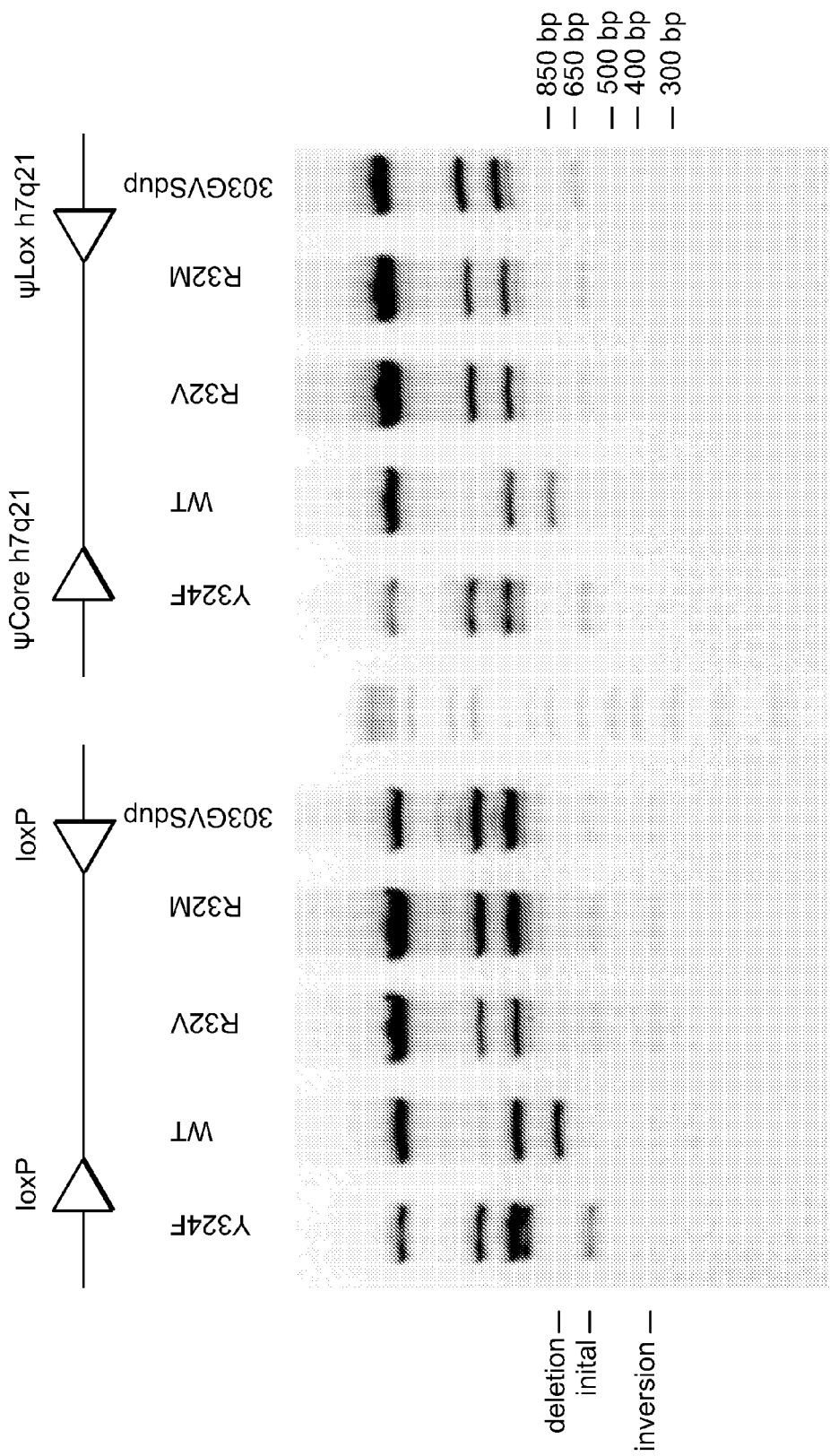
FIG. 5A is a gel image.
Figure 5C:
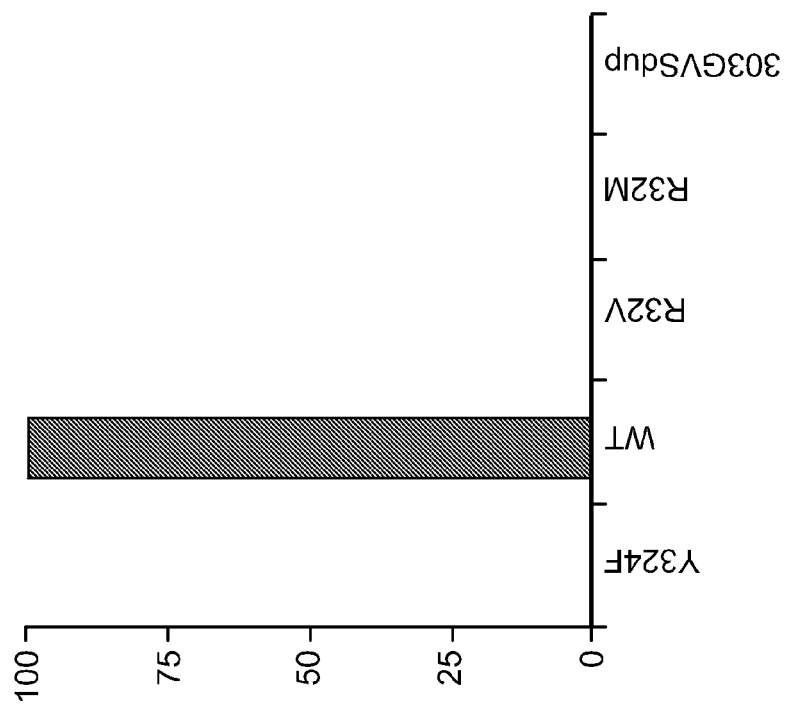
FIG. 5C is a graph of % in vivo recombination versus deletion or inversion.
Figure 5B:
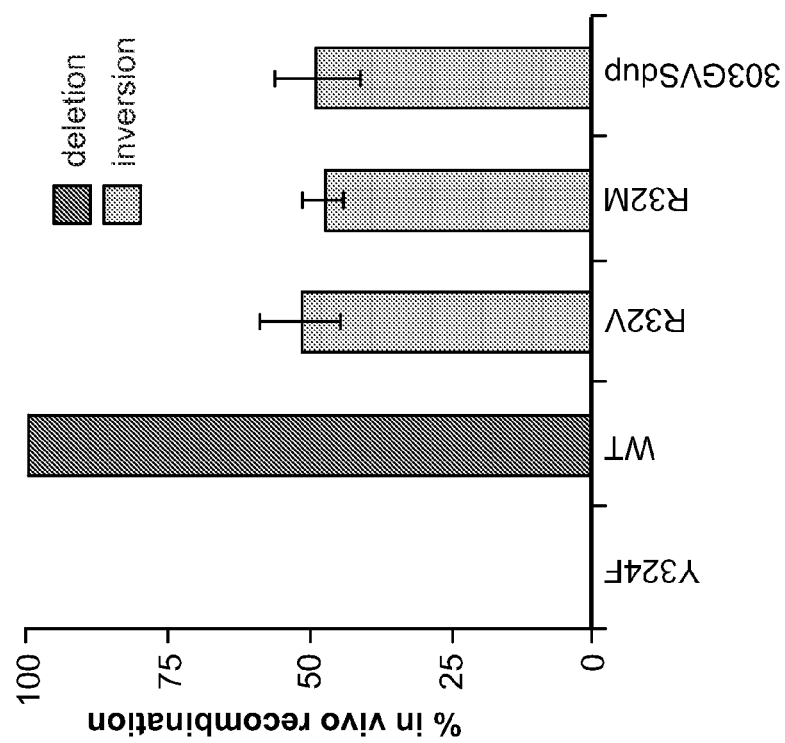
FIG. 5B is a graph of % in vivo recombination versus deletion or inversion.

FIG. 5 depicts recombination of recombination-site carrying plasmids by mutants of Cre. FIG. 5A shows digest analysis of loxP/loxP (left five lanes) and φlox h7q21/φCore h7q21 (right five lanes) recombination. FIGS. 5B and 5C depict inversion and recombination frequency of loxP/loxP and φCore h7q21/φlox h7q21 recombination, respectively. Error bars correspond to 95% C.I. (n=2 independent experiment).

Achieving equilibrium in the inversion assay should result in 50% inverted products. Recombination of two loxP sites by R32V, R32M, and 303GVSdup yielded approximately 50% inversion. In contrast, all detectable WT products were deletions (FIGS. 5A & 5B). In a dividing cell, excision events may be fixed in the population because of dilution of the excised product by cell replication and the difficulty in reversing the reaction due to its intermolecular nature. All substrate plasmids experienced at least one excision event during 12 hours of growth.

To test the mutants for improved accuracy, their ability was tested to recombine a known human pseudo-loxP site φLox h7q21 and φCore h7q21, which consists of inverted repeats from loxP but a spacer that matches φLox h7q21F (FIG. 2). WT improperly excised 100% of the substrate, while R32V, R32M, and 303GVSdup produced no detectable recombination products (FIGS. 5A & 5C). In aggregate, the data provide evidence that the isolated mutants are better able to distinguish on-target and off-target sites than WT.

R32V, R32M, and 303GVSdup have improved accuracy in a genomic context. One explanation for the improved accuracy with R32V, R32M, and 303GVSdup is that the mutants simply altered the preferred off-target sites without changing the overall accuracy. To test this possibility, the efficiency of off-target insertions across the entire E. coli genome was measured. Strains carrying the arabinose-inducible expression plasmids were transformed with a plasmid containing a loxP site, the kanamycin resistance gene, and R6 k gamma, an origin of replication that does not function in the absence of the pir gene product. Successful insertion of the loxP site into the genome would result in the maintenance of resistance to kanamycin. To control for variation in the transformation efficiency, the number of R6 k gamma colonies was normalized by the number of colonies arising from transformation with a replication-competent plasmid lacking loxP.

The cells were briefly pulsed with arabinose prior to the growth on LB/glucose and a WT-mediated integration frequency of 1.3×10-4 was obtained. As shown in Table 1 below.

|  | loxP+ ori- kanR colonies | loxP- ori+ kanR colonies | loxP insertion frequency | 95% C.I. |
|---|---|---|---|---|
| Y324F | 1 | $6.2 \times 10^6$ | $1.6 \times 10^{-7}$ | $0\text{-}4.8 \times 10^{-7}$ |
| WT | 1,025 | $8.1 \times 10^6$ | $1.3 \times 10^{-4}$ | $1.2 \times 10^{-4}\text{-}1.4 \times 10^{-4}$ |
| R32V | 2 | $9.4 \times 10^6$ | $2.1 \times 10^{-7}$ | $0\text{-}5.1 \times 10^{-7}$ |
| R32M | 3 | $6.3 \times 10^7$ | $4.8 \times 10^{-8}$ | $0\text{-}1 \times 10^{-7}$ |
| 303GVSdup | 46 | $2.6 \times 10^7$ | $1.7 \times 10^{-6}$ | $1.2 \times 10^{-6}\text{-}2.2 \times 10^{-6}$ |

Table 1 shows genome-wide off-target integration frequency. Insertion frequency corresponds to the ratio of loxP+ to loxP− colonies. 95% C.I. were computed using the Poisson variance. The data represent pooled observations from 3-4 independent experiments.

303GVSdup had an integration frequency ~100-fold lower than WT. The integration frequencies of R32V and R32M were lower than that of 303GVSdup and could not be distinguished from Y324F background given the resolution of the assay. These data strongly suggest that the higher accuracy of the mutants was not restricted to only loxBait and φLox h7q21.

The invention is further illustrated by the following example, which should not be construed as limiting. The contents of all references, patents and published patent applications cited throughout this application are hereby incorporated by reference in their entirety for all purposes.

Example I

Selection for Functional loxP Variants and Measurement of their Recombination Efficiency Libraries of half-site variants were constructed by performing extension PCR on the entire pZE21G plasmid[67] such that the amplification product was 2,437 bp long and contained a loxP site and a random library site near each end. The libraries were purified using the QIAquick PCR Purification Kit (Qiagen), 10-20 ng of the DNA was treated with 1 U Cre (New England Biolabs) in Cre reaction buffer (10 mM MgCl2, 33 mM NaCl, 50 mM Tris-HCl pH 7.5) in 20 µL total reaction volume for 1 hr at 37° C., heat inactivated at 75-80° C., then digested with DpnI. The DNA was then purified, digested with PlasmidSafe (Epicentre), and transformed into One Shot Top10 chemically competent cells (Invitrogen). Colonies were randomly selected for sequencing. Substrates for validating the selection hits were generated by performing extension PCR on pZE21G as for the selections except that sequences obtained from the selection were in place of the random library. 30 ng of purified products were treated with 1 U Cre in Cre reaction buffer in 20 µL total reaction volume for 1.5 hr at 37° C. followed by heat inactivation of the enzyme. The entire reaction was resolved on a 0.7% agarose gel stained with SYBR Green I (Invitrogen). Each recombination was performed in parallel with a no-enzyme negative control.

Example II

Negative and Positive Selection

The positive selection substrate pCR-(loxP-ampR-loxP-inv)inv was built by amplifying ampR from pQL123[68] using extension PCR which flanked the gene with loxP sites in inverse orientation relative to each other, and TOPO cloning the product pCR-Blunt II-TOPO (Invitrogen). Sequencing was used to screen for colonies in which the ampR gene was in reverse orientation with respect to the promoter. A similar workflow was used to build the pCR-loxBait-ampR-loxP negative selection substrate, which contained the loxP/lox-Bait flanked ampR gene in frame with the promoter. Both selection plasmids were maintained in NEB 10-beta cells (recA1 araD139 Δ(ara-leu)7697); cells were made electrocompetent using standard techniques[69]. The Cre gene was obtained from pQL123, though the alanine at the second position was reverted to the serine found in WT Cre (GenBank sequence YP_006472). Control expression were cloned by replacing the HpaII gene in pARC8-HpaII[70] with Cre or Cre(Y324F) using Gibson assembly[71].

A library of Cre variants was generated by mutagenic PCR using a pool of 19 oligos that substituted each of the 19 codons encoding S20-S38 for NNN. The library was introduced into pARC8 using Gibson assembly, desalted by drop dialysis, and electroporated into competent cells carrying pCR-(loxP-ampR-loxPinv)inv. Control transformations were performed with 100 pg pARC8-Cre and pARC8-Y324F. Transformed cells were recovered in low-salt 2×LB (2% bacto-tryptone, 1% yeast extract, 0.5% NaCl, pH 7.5) at 37° C. for 30 min, induced with 0.2% arabinose at 37° C. for 30 min, and recovered in SOC+200 µM IPTG fat 37° C. for 1 hr. The cells were then grown overnight at 37° C. on LB+0.2% glucose+100 µM IPTG+12.5 µg/mL chloramphenicol+50 µg/mL kanamycin plates either with or without 100 µg/mL carbenicillin.

Colonies obtained from the positive selection of the library and of the controls were collected by scraping. DNA was isolated using the QIAprep Spin Miniprep kit (Qiagen) and was digested with XmaI and SpeI (which cut only the substrate plasmids.) The concentration of expression plasmid was quantified via agarose gels. Electrocompetent cells carrying the pCR-loxBait-ampR-loxP negative selection substrate were transformed with 100 pg of the expression plasmid, recovered the cells in low-salt 2×LB for at 28° C. for 30 min, induced with 0.2% arabinose at 28° C. for 30 min, washed with SOC, and recovered in SOC+200 µM IPTG at 37° C. for 1 hr. The cells were then grown overnight at 37° C. on LB+0.2% glucose+100 µM IPTG+12.5 µg/mL chloramphenicol+50 µg/mL kanamycin+100 µg/mL carbenicillin plates. To ensure clonality, the isolated variants were amplified and re-cloned into pARC8 via Gibson assembly.

Example III

In Vivo Quantification of Mutants' Recombination Efficiencies

The loxP/loxP recombination substrate pZE2-loxP/loxP was obtained by cloning the XhoI/BamHI fragment from pCR-(loxP-ampR-loxPinv)inv into XhoI/BamHI-digested pZE21G. The φCore h7q21/φlox h7q21 recombination substrate pZE2-φCore h7q21/φlox h7q21 was also built by cloning into pCR-TOPO II-Blunt, screening for the inverted orientation, and subcloning into pZE21G.

Efficiencies were measured by co-transforming equimolar amounts of a pARC8-based expression plasmid (WT, Y324F, R32V, R32M, or 303GVSdup) and either pZE2-loxP/loxP or pZE2-φCore h7q21/φlox h7q21 into OneShot Top10 chemically competent cells (recA1 araD139 Δ(ara-leu)7697). The cells were recovered in LB+0.2% glucose at 37° C. for 1 hr, then grown at 37° C. for 12 hrs in LB+0.2% glucose+12.5 µg/mL chloramphenicol+50 µg/mL kanamycin. The plasmids were isolated using the QIAprep Spin Miniprep kit, digested with ScaI-HF and NcoI-HF (both from New England Biolabs), and quantified on 1% agarose gels.

Example IV

Genome-Wide Off-Target Integration Assay

Electrocompetent cells were prepared from each of the pARC8-based expression plasmids (WT, Y324F, R32V, R32M, or 303GVSdup) cloned in NEB 10-beta cells using 40 mL of culture per transformation. Each expression strain was transformed either with 200 ng pUNI1068 (loxP+, oriR6Kγ) or an equimolar amount of pZE21G (loxP+, oriColE1). The two transformations were done in parallel using competent cells made from aliquots of the same culture. The cells were recovered in LB for at 37° C. for 30 min, induced with 0.2% arabinose at 37° C. for 30 min, and recovered in SOC at 37° C. for 1 hr. The cells were then grown overnight at 37° C. on LB+0.2% glucose+12.5 µg/mL chloramphenicol+50 µg/mL kanamycin plates.

REFERENCES

The following references are hereby incorporated by reference in their entireties for all purposes.
1. Stocking, C. et al. Distinct classes of factor-independent mutant can be isolated after retroviral mutagenesis of a human myeloid stem cell line. Growth Factors 8, 197-209 (1993).
2. Li, Z. et al. Murine Leukemia Induced by Retroviral Gene Marking. Science 296, 497-497 (2002).
3. Hacein-Bey-Abina, S. et al. A Serious Adverse Event after Successful Gene Therapy for X-Linked Severe Combined Immunodeficiency. New England Journal of Medicine 348, 255-256 (2003).
4. Rouet, P., Smih, F. & Jasin, M. Introduction of double-strand breaks into the genome of mouse cells by expression of a rare-cutting endonuclease. Molecular and Cellular Biology 14, 8096-8106 (1994).
5. Chevalier, B. S. et al. Design, activity, and structure of a highly specific artificial endonuclease. Molecular Cell 10, 895-905 (2002).
6. Kim, Y. G., Cha, J. & Chandrasegaran, S. Hybrid restriction enzymes: zinc finger fusions to Fok I cleavage domain. Proceedings of the National Academy of Sciences 93, 1156-1160 (1996).
7. Li, T. et al. TAL nucleases (TALNs): hybrid proteins composed of TAL effectors and FokI DNA-cleavage domain. Nucleic Acids Research 39, 359-372 (2010).
8. Christian, M. et al. Targeting DNA double-strand breaks with TAL effector nucleases. Genetics 186, 757-761 (2010).
9. Cong, L. et al. Multiplex Genome Engineering Using CRISPR/Cas Systems. Science (2013).doi:10.1126/science.1231143
10. Mali, P. et al. RNA-Guided Human Genome Engineering via Cas9. Science (2013).doi:10.1126/science.1232033
11. Mao, Z., Bozzella, M., Seluanov, A. & Gorbunova, V. Comparison of nonhomologous end joining and homologous recombination in human cells. Journal of Molecular Biology 7, 1765-1771 (2008).
12. Hartlerode, A. J. & Scully, R. Mechanisms of double-strand break repair in somatic mammalian cells. Biochemical Journal 423, 157-168 (2009).

13. Grindley, N. D. F., Whiteson, K. L. & Rice, P. A. Mechanisms of Site-Specific Recombination. Annual Review of Biochemistry 75, 567-605 (2006).
14. Buchholz, F. & Stewart, A. F. Alteration of Cre recombinase site specificity by substrate-linked protein evolution. Nature Biotechnology 19, 1047-1052 (2001).
15. Sclimenti, C. R., Thyagarajan, B. & Calos, M. P. Directed evolution of a recombinase for improved genomic integration at a native human sequence. Nucleic Acids Research 29, 5044-5051 (2001).
16. Santoro, S. W. & Schultz, P. G. Directed evolution of the site specificity of Cre recombinase. Proceedings of the National Academy of Sciences 99, 4185-4190 (2002).
17. Akopian, A., He, J., Boocock, M. R. & Stark, W. M. Chimeric recombinases with designed DNA sequence recognition. Proceedings of the National Academy of Sciences 100, 8688-8691 (2003).
18. Gordley, R. M., Smith, J. D., Gräslund, T. & Barbas, C. F., III Evolution of Programmable Zinc Finger-recombinases with Activity in Human Cells. Journal of Molecular Biology 367, 802-813 (2007).
19. Sarkar, I., Hauber, I., Hauber, J. & Buchholz, F. HIV-1 proviral DNA excision using an evolved recombinase. Science 316, 1912-1915 (2007).
20. Keravala, A. et al. Mutational derivatives of PhiC31 integrase with increased efficiency and specificity. Molecular Therapy 17, 112-120 (2009).
21. Gersbach, C. A., Gaj, T., Gordley, R. M. & Barbas, C. F. Directed evolution of recombinase specificity by split gene reassembly. Nucleic Acids Research 38, 4198-4206 (2010).
22. Abi-Ghanem, J. et al. Engineering of a target site-specific recombinase by a combined evolution- and structure-guided approach. Nucleic Acids Research (2012).doi: 10.1093/nar/gks1308
23. Mercer, A. C., Gaj, T., Fuller, R. P. & Barbas, C. F. Chimeric TALE recombinases with programmable DNA sequence specificity. Nucleic Acids Research 40, 11163-11172 (2012).
24. Thyagarajan, B., Guimarães, M. J., Groth, A. C. & Calos, M. P. Mammalian genomes contain active recombinase recognition sites. Gene 244, 47-54 (2000).
25. Thyagarajan, B., Olivares, E. C., Hollis, R. P., Ginsburg, D. S. & Calos, M. P. Site-specific genomic integration in mammalian cells mediated by phage phiC31 integrase. Molecular and Cellular Biology 21, 3926-3934 (2001).
26. Olivares, E. C., Hollis, R. P. & Calos, M. P. Phage R4 integrase mediates site-specific integration in human cells. Gene 278, 167-176 (2001).
27. Chalberg, T. W. et al. Integration specificity of phage phiC31 integrase in the human genome. Journal of Molecular Biology 357, 28-48 (2006).
28. Keravala, A. et al. A diversity of serine phage integrases mediate site-specific recombination in mammalian cells. Molecular Genetics and Genomics 276, 135-146 (2006).
29. Semprini, S. et al. Cryptic loxP sites in mammalian genomes: genome-wide distribution and relevance for the efficiency of BAC/PAC recombineering techniques. Nucleic Acids Research 35, 1402-1410 (2007).
30. Nelson, H. C. M. & Sauer, R. T. Lambda repressor mutations that increase the affinity and specificity of operator binding. Cell 42, 549-558 (1985).
31. Nelson, H. C. M. & Sauer, R. T. Interaction of mutant λ repressors with operator and non-operator DNA. Journal of Molecular Biology 192, 27-38 (1986).
32. Sternberg, N. & Hamilton, D. Bacteriophage P1 site-specific recombination. I. Recombination between loxP sites. Journal of Molecular Biology 150, 467-486 (1981).
33. Hoess, R. H., Ziese, M. & Sternberg, N. P1 site-specific recombination: nucleotide sequence of the recombining sites. Proceedings of the National Academy of Sciences 79, 3398-3402 (1982).
34. Abremski, K. & Hoess, R. Bacteriophage P1 site-specific recombination. Purification and properties of the Cre recombinase protein. The Journal of Biological Chemistry 259, 1509-1514 (1984).
35. Van Duyne, G. D. A structural view of cre-loxp site-specific recombination. Annual Reviews of Biophysics and Biomolecular Structure 30, 87-104 (2001).
36. Hartung, M. & Kisters-Woike, B. Cre mutants with altered DNA binding properties. The Journal of Biological Chemistry 273, 22884-22891 (1998).
37. Missirlis, P. I., Smailus, D. E. & Holt, R. A. A high-throughput screen identifying sequence and promiscuity characteristics of the loxP spacer region in Cre-mediated recombination. BMC Genomics 7, 73 (2006).
38. Sheren, J., Langer, S. J. & Leinwand, L. A. A randomized library approach to identifying functional lox site domains for the Cre recombinase. Nucleic Acids Research 35, 5464-5473 (2007).
39. Rüfer, A., Neuenschwander, P. F. & Sauer, B. Analysis of Cre-loxP interaction by surface plasmon resonance: Influence of spermidine on cooperativity. Analytical Biochemistry 308, 90-99 (2002).
40. Jen-Jacobson, L. Protein-DNA recognition complexes: conservation of structure and binding energy in the transition state. Biopolymers 44, 153-180 (1997).
41. Guo, F., Gopaul, D. & Van Duyne, G. Structure of Cre recombinase complexed with DNA in a site-specific recombination synapse. Nature (1997).
42. Gopaul, D. N., Guo, F. & Van Duyne, G. D. Structure of the Holliday junction intermediate in Cre-loxP site-specific recombination. The EMBO Journal 17, 4175-4187 (1998).
43. Cornu, T. I. et al. DNA-binding Specificity Is a Major Determinant of the Activity and Toxicity of Zinc-finger Nucleases. Molecular Therapy 16, 352-358 (2007).
44. Ringrose, L. et al. Comparative kinetic analysis of FLP and cre recombinases: mathematical models for DNA binding and recombination. Journal of Molecular Biology 284, 363-384 (1998).
45. Miller, J. C. et al. An improved zinc-finger nuclease architecture for highly specific genome editing. Nature Biotechnology 25, 778-785 (2007).
46. Szczepek, M. et al. Structure-based redesign of the dimerization interface reduces the toxicity of zinc-finger nucleases. Nature Biotechnology 25, 786-793 (2007).
47. Aranda, M. et al. Altered directionality in the cre-loxP site-specific recombination pathway. Journal of Molecular Biology 311, 453-459 (2001).
48. Livet, J. et al. Transgenic strategies for combinatorial expression of fluorescent proteins in the nervous system. Nature 450, 56-62 (2007).
49. Friedland, A. E. et al. Synthetic gene networks that count. Science 324, 1199-1202 (2009).
50. Nagy, A. Cre recombinase: the universal reagent for genome tailoring. Genesis 26, 99-109 (2000).
51. Branda, C. S. & Dymecki, S. M. Talking about a revolution: The impact of site-specific recombinases on genetic analyses in mice. Developmental Cell 6, 7-28 (2004).

52. Turan, S. & Bode, J. Site-specific recombinases: from tag-and-target- to tag-and-exchange-based genomic modifications. The FASEB Journal 25, 4088-4107 (2011).
53. Schmidt, E. E., Taylor, D. S., Prigge, J. R., Barnett, S. & Capecchi, M. R. Illegitimate Cre-dependent chromosome rearrangements in transgenic mouse spermatids. Proceedings of the National Academy of Sciences 97, 13702-13707 (2000).
54. Heidmann, D. & Lehner, C. F. Reduction of Cre recombinase toxicity in proliferating Drosophila cells by estrogen-dependent activity regulation. Development Genes and Evolution 211, 458-465 (2001).
55. Loonstra, A. et al. Growth inhibition and DNA damage induced by Cre recombinase in mammalian cells. Proceedings of the National Academy of Sciences 98, 9209-9214 (2001).
56. Silver, D. P. & Livingston, D. M. Self-excising retroviral vectors encoding the Cre recombinase overcome Cre-mediated cellular toxicity. Molecular Cell 8, 233-243 (2001).
57. Coppoolse, E. R. et al. Cre recombinase expression can result in phenotypic aberrations in plants. Plant Molecular Biology 51, 263-279 (2003).
58. Lee, J.-Y. et al. RIP-Cre revisited, evidence for impairments of pancreatic beta-cell function. The Journal of Biological Chemistry 281, 2649-2653 (2006).
59. Buerger, A. et al. Dilated cardiomyopathy resulting from high-level myocardial expression of Cre-recombinase. Journal of Cardiac Failure 12, 392-398 (2006).
60. Forni, P. E. et al. High levels of Cre expression in neuronal progenitors cause defects in brain development leading to microencephaly and hydrocephaly. The Journal of Neuroscience 26, 9593-9602 (2006).
61. Naiche, L. A. & Papaioannou, V. E. Cre activity causes widespread apoptosis and lethal anemia during embryonic development. Genesis 45, 768-775 (2007).
62. Huh, W. J., Mysorekar, I. U. & Mills, J. C. Inducible activation of Cre recombinase in adult mice causes gastric epithelial atrophy, metaplasia, and regenerative changes in the absence of 'floxed' alleles. American Journal of Physiology—Gastrointestinal and Liver Physiology 299, G368-80 (2010).
63. Zhu, J., Nguyen, M.-T., Nakamura, E., Yang, J. & Mackem, S. Cre-mediated recombination can induce apoptosis in vivo by activating the p53 DNA damage-induced pathway. Genesis 50, 102-111 (2012).
64. Feil, R. et al. Ligand-activated site-specific recombination in mice. Proceedings of the National Academy of Sciences 93, 10887-10890 (1996).
65. Kellendonk, C. et al. Regulation of Cre recombinase activity by the synthetic steroid RU 486. Nucleic Acids Research 24, 1404-1411 (1996).
66. Jullien, N., Sampieri, F., Enjalbert, A. & Herman, J.-P. Regulation of Cre recombinase by ligand-induced complementation of inactive fragments. Nucleic Acids Research 31, e131 (2003).
67. Isaacs, F. J. et al. Engineered riboregulators enable post-transcriptional control of gene expression. Nature Biotechnology 22, 841-847 (2004).
68. Liu, Q., Li, M. Z., Leibham, D., Cortez, D. & Elledge, S. J. The univector plasmid-fusion system, a method for rapid construction of recombinant DNA without restriction enzymes. Current Biology 8, 1300-1309 (1998).
69. Sambrook, J. & Russell, D. W. Molecular Cloning: a Laboratory Manual (2001).
70. Meister, G. E., Chandrasegaran, S. & Ostermeier, M. Heterodimeric DNA methyltransferases as a platform for creating designer zinc finger methyltransferases for targeted DNA methylation in cells. Nucleic Acids Research 38, 1749-1759 (2010).
71. Gibson, D. G. et al. Enzymatic assembly of DNA molecules up to several hundred kilobases. Nature Methods 6, 343-345 (2009).

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A mutant of Cre recombinase comprising a Cre recombinase with an R to V mutation at residue 32 (R32V), an R to M mutation at residue 32 (R32M), or a de novo duplication of residues 303-305 (303GVSdup) compared to a wild type Cre recombinase isolated from a P1 bacteriophage.

2. The mutant of Cre recombinase of claim 1 wherein the mutant Cre recombinase comprises an R to V mutation at residue 32 (R32V) compared to the wild type Cre recombinase isolated from a P1 bacteriophage.

3. The mutant of Cre recombinase of claim 1 wherein the mutant Cre recombinase comprises an R to M mutation at residue 32 (R32M) compared to the wild type Cre recombinase isolated from a P1 bacteriophage.

4. The mutant of Cre recombinase of claim 1 wherein the mutant Cre recombinase comprises a de novo duplication of residues 303-305 (303GVSdup) compared to the wild type Cre recombinase isolated from a P1 bacteriophage.

5. The mutant of Cre recombinase of claim 1 wherein the mutant Cre recombinase is less active at off-target sites compared to the wild type Cre recombinase.

6. A method of recombining loxP sites comprising contacting a mutant of Cre recombinase of claim 1 with the loxP sites.

7. A method of destabilizing cooperative binding of DNA-binding proteins comprising contacting mutant of Cre recombinase of claim 1 with a DNA binding protein.

* * * * *